US012589264B2

(12) United States Patent
Li et al.

(10) Patent No.: US 12,589,264 B2
(45) Date of Patent: Mar. 31, 2026

(54) ULTRASONIC TREATMENT DEVICE

(71) Applicant: SHENZHEN PENINSULA MEDICAL GROUP, Shenzhen (CN)

(72) Inventors: Yanan Li, Shenzhen (CN); Yujia Peng, Shenzhen (CN); Xiaobing Lei, Shenzhen (CN); Yi Ding, Shenzhen (CN); Lin Mi, Shenzhen (CN)

(73) Assignee: SHENZHEN PENINSULA MEDICAL GROUP, Shenzhen (CN)

( * ) Notice: Subject to any disclaimer, the term of this patent is extended or adjusted under 35 U.S.C. 154(b) by 0 days.

(21) Appl. No.: 18/826,479

(22) Filed: Sep. 6, 2024

(65) Prior Publication Data

US 2024/0424321 A1 Dec. 26, 2024

Related U.S. Application Data

(63) Continuation of application No. PCT/CN2024/088895, filed on Apr. 19, 2024.

(30) Foreign Application Priority Data

Apr. 20, 2023 (CN) .......................... 202320974770.0
Apr. 16, 2024 (CN) .......................... 202410457456.4

(51) Int. Cl.
*A61N 7/02* (2006.01)
*A61N 7/00* (2006.01)

(52) U.S. Cl.
CPC ........ *A61N 7/02* (2013.01); *A61N 2007/0078* (2013.01)

(58) Field of Classification Search
CPC .............. A61N 7/02; A61N 2007/0078; A61N 2007/0034; A61F 7/007; A61F 2007/0052; A61F 2007/0056; A61F 2007/0095
See application file for complete search history.

(56) References Cited

U.S. PATENT DOCUMENTS

2009/0299180 A1* 12/2009 Lacoste .................... A61N 7/02
600/449
2011/0040235 A1 2/2011 Castel
(Continued)

FOREIGN PATENT DOCUMENTS

CN 101468240 A 7/2009
CN 104353194 A 2/2015
(Continued)

OTHER PUBLICATIONS

International Search Report and Written Opinion issued in corresponding PCT Application No. PCT/CN2024/088895, dated Jul. 23, 2024.
(Continued)

*Primary Examiner* — Bo Joseph Peng
(74) *Attorney, Agent, or Firm* — Westbridge IP LLC

(57) ABSTRACT

An ultrasonic treatment device includes an ultrasonic treatment tip and a cooling mechanism. The ultrasonic treatment tip includes a sealed cavity, a sound-transferring medium disposed inside the sealed cavity, a treatment window and a heat-transferring surface. The ultrasonic treatment tip is configured for outputting ultrasonic waves to a treatment area through the treatment window. The heat-transferring surface is intimately surrounding the treatment window and thermally contacted with the treatment area. The cooling mechanism is configured to discharge heat generated at the treatment area outside of the ultrasonic device by thermally contacting the heat-transferring surface.

14 Claims, 5 Drawing Sheets

(56)  References Cited

U.S. PATENT DOCUMENTS

| | | |
|---|---|---|
| 2011/0077555 A1 | 3/2011 | Wing et al. |
| 2013/0131704 A1* | 5/2013 | Pechoux .................. A61N 7/02 606/169 |
| 2016/0089550 A1* | 3/2016 | DeBenedictis .......... A61N 7/02 601/3 |
| 2019/0009110 A1 | 1/2019 | Gross et al. |

FOREIGN PATENT DOCUMENTS

| | | |
|---|---|---|
| CN | 217286923 U | 8/2022 |
| CN | 115531750 A | 12/2022 |
| CN | 220125370 U | 12/2023 |
| EP | 3922200 A1 | 12/2021 |
| JP | H08131454 A | 5/1996 |
| JP | 2013512016 A | 4/2013 |
| KR | 20130137256 A | 12/2013 |
| KR | 20200000754 A | 1/2020 |
| WO | 2023033230 A1 | 3/2023 |

OTHER PUBLICATIONS

European Search Report issued in counterpart European Patent Application No. EP 24792139.8, dated Dec. 8, 2025.
Notice of Reasons for Refusal issued in counterpart Japanese Patent Application No. 2024-577311, dated Dec. 2, 2025.

* cited by examiner

ULTRASONIC TREATMENT DEVICE

CROSS-REFERENCE TO RELATED APPLICATIONS

The present application is a continuation application of International Application No. PCT/CN2024/088895, filed on Apr. 19, 2024, which claims priority to Chinese Patent Application No. 202320974770.0, filed on Apr. 20, 2023, and Chinese Patent Application No. 202410457456.4, filed on Apr. 16, 2024. The disclosures of the above-mentioned applications are incorporated herein by reference in their entireties.

TECHNICAL FIELD

The present application relates to the technical field of ultrasonic treatment devices, and in particular to an ultrasonic treatment device.

BACKGROUND

When the ultrasonic treatment device treats the treatment area, the temperature of the skin at the treatment area will rise. The temperature of the inner layer of the skin at the treatment area will reach about 70° C., and the temperature of the surface layer of the skin at the treatment area will reach about 50° C. If the heat is not dissipated in time, it may cause discomfort to the patient's treatment area, and may even cause burns to the patient's surface skin at the treatment area.

SUMMARY

The main purpose of the present application is to provide an ultrasonic treatment device, aiming to reduce the temperature at the treatment area.

In view of the above objectives, the present application provides an ultrasonic treatment device, including:

an ultrasonic treatment tip, including a sealed cavity, a sound-transferring medium disposed inside the sealed cavity, a treatment window and a heat-transferring surface; the ultrasonic treatment tip being configured for outputting ultrasonic waves to a treatment area through the treatment window; the heat-transferring surface being intimately surrounding the treatment window, and thermally contacted with the treatment area; and a cooling mechanism, configured to discharge heat generated at the treatment area outside of the ultrasonic device by thermally contacting the heat-transferring surface.

In an embodiment, the cooling mechanism includes a semiconductor cooling assembly, and the semiconductor cooling assembly includes a semiconductor cooling sheet, a heat-transferring member and a heat-dissipating member; a cold end of the semiconductor cooling sheet is tightly attached with the heat-transferring surface, and a hot end of the semiconductor cooling sheet is tightly attached with the heat-transferring member; a heat exchange end of the heat-transferring member away from the semiconductor cooling sheet is connected to the heat-dissipating member.

In an embodiment, the heat-dissipating member is configured as a heat-dissipating sheet.

In an embodiment, the ultrasonic treatment device further includes a handle.

The handle is connected to a connection end of the ultrasonic treatment tip away from the heat-transferring surface, and the heat-dissipating member is disposed within the handle; the heat exchange end is provided at the connection end, and the heat exchange end is abutted against the heat-dissipating member.

In an embodiment, the semiconductor cooling assembly further includes a heat-dissipating fan, and the heat-dissipating fan is provided at one side of the heat-dissipating member.

In an embodiment, the cooling mechanism includes a semiconductor cooling assembly, and the semiconductor cooling assembly includes a semiconductor cooling sheet; a cold end of the semiconductor cooling sheet tightly is attached with the heat-transferring surface, and a hot end of the semiconductor cooling sheet is tightly attached with the sealed cavity.

In an embodiment, the cooling mechanism includes a water cooling assembly, and the water cooling assembly includes a water cooling cavity, a water inlet channel and a water outlet channel; the water cooling cavity is provided inside a shell of the ultrasonic treatment tip and close to the heat-transferring surface; the water inlet channel is communicated with the water cooling cavity, and the water outlet channel is communicated with the water cooling cavity.

In an embodiment, the water inlet channel and the water outlet channel are provided at an inner side of the shell of the ultrasonic treatment tip.

In an embodiment, the ultrasonic treatment device further includes a handle.

A connection end of the ultrasonic treatment tip away from the heat-transferring surface is provided with a hook, a water inlet pipe section and a water outlet pipe section, and the water inlet pipe section is communicated with the water inlet channel; the water outlet pipe section is communicated with the water outlet channel, and the handle of the ultrasonic treatment device is configured to snap on the hook to connect the connection end of the ultrasonic treatment tip.

In an embodiment, the water inlet channel is disposed away from the water outlet channel.

In an embodiment, the cooling mechanism includes a heat-transferring member and a semiconductor cooling sheet; one end of the heat-transferring member is attached with the semiconductor cooling sheet, and the other end of the heat-transferring member is in thermal contact with the heat-transferring surface; the semiconductor cooling sheet is thermally connected to the heat-transferring surface through the heat-transferring member.

A working current of the semiconductor cooling sheet includes a first direction current and a second direction current; the first direction current and the second direction current have opposite current directions; in response to that the working current of the semiconductor cooling sheet is the first direction current, an end of the semiconductor cooling sheet in attachment with the heat-transferring member is a hot end; and in response to that the working current of the semiconductor cooling sheet is the second direction current, an end of the semiconductor cooling sheet in attachment with the heat-transferring member is a cold end.

In an embodiment, on and off states of the semiconductor cooling sheet are switchable by a switch provided in the ultrasonic treatment device.

In an embodiment, the ultrasonic treatment tip is provided with an outer shell and an inner shell; the inner shell is provided in a cavity of the outer shell, and an ultrasonic cavity is provided in the inner shell; an ultrasonic transducer unit is provided in the ultrasonic cavity, and the ultrasonic transducer unit is configured to emit ultrasonic waves toward the treatment window.

The inner shell is provided with a first end face and a second end face opposite with each other; the treatment window is provided at the first end face, and the treatment window is tightly attached with the heat-transferring surface; an outer wall of the inner shell is spaced from an inner wall of the outer shell to form a heat-insulating cavity, and a heat-insulating member is disposed in the heat-insulating cavity.

In an embodiment, the ultrasonic transducer unit includes one ultrasonic transducer, and the ultrasonic transducer is movable in the ultrasonic cavity and is configured to emit ultrasonic waves toward the heat-transferring surface.

In an embodiment, the ultrasonic transducer unit includes a plurality of ultrasonic transducers, and the plurality of ultrasonic transducers are provided in the ultrasonic cavity in an array and are configured to emit ultrasonic waves toward the heat-transferring surface.

In an embodiment, the ultrasonic treatment tip further includes a controller and a temperature sensor configured to sense temperature of the heat-transferring surface; the temperature sensor is electrically connected to the controller to feedback a detected temperature to the controller in real time, and the controller is configured to control the cooling mechanism.

The present application further provides a method for controlling an ultrasonic treatment device, including controlling a working current of the semiconductor cooling sheet to be a first direction current during at least partial working period of the ultrasonic treatment device, to make ultrasonic energy and heat of the semiconductor cooling sheet at least partially overlapped and acted on a same target tissue.

In an embodiment, in a process of emitting ultrasonic energy, the ultrasonic treatment device performs following operations:

obtaining a real time treatment parameter of a target tissue;

determining whether the real time treatment parameter is less than a first treatment parameter;

in response to that the real time treatment parameter is less than the first treatment parameter, controlling the working current of the semiconductor cooling sheet to be the first direction current;

in response to that the real time treatment parameter is not less than the first treatment parameter, determining whether the real time treatment parameter is greater than a second treatment parameter;

in response to that the real time treatment parameter is greater than the second treatment parameter, controlling the working current of the semiconductor cooling sheet to be the second direction current; and in response to that the real time treatment parameter is not greater than the second treatment parameter, controlling the working current of the semiconductor cooling sheet to be the first direction current.

In an embodiment, the ultrasonic treatment device is provided with a first working mode and a second working mode; in response to that the ultrasonic treatment device is in the first working mode, the ultrasonic treatment device is configured to emit ultrasonic energy to a target tissue, and the working current of the semiconductor cooling sheet is the first direction current; in response to that the ultrasonic treatment device is in the second working mode, the ultrasonic treatment device is configured to emit ultrasonic energy to the target tissue, and the working current of the semiconductor cooling sheet is a second direction current.

A working sequence of the ultrasonic treatment device includes a first working sequence only, or at least includes the first working sequence and the second working sequence.

In the first working sequence of the ultrasonic treatment device, the ultrasonic treatment device is controlled to enter the first working mode, and in the second working sequence of the ultrasonic treatment device, the ultrasonic treatment device is controlled to enter the second working mode.

In an embodiment, the ultrasonic treatment device is provided with a first working period before emitting ultrasonic energy and/or a third working period after emitting ultrasonic energy.

In the first working period, the working current of the semiconductor cooling sheet is controlled to be the first direction current or a second direction current; in the third working period, the working current of the semiconductor cooling sheet is controlled to be the first direction current or the second direction current.

In an embodiment, the ultrasonic treatment device further performs following operations in the third working period:

determining whether a real time temperature of a target tissue is lower than a first temperature threshold; and in response to that the real time temperature of the target tissue is lower than the first temperature threshold, cutting off or reducing the working current of the semiconductor cooling sheet.

The above-mentioned ultrasonic treatment device includes at least the following beneficial effects.

The technical solution of the present application adopts an ultrasonic treatment tip and a cooling mechanism. The ultrasonic treatment device includes: an ultrasonic treatment tip and a cooling mechanism. The ultrasonic treatment tip includes a sealed cavity, a sound-transferring medium disposed inside the sealed cavity, a treatment window and a heat-transferring surface. The ultrasonic treatment tip is configured for outputting ultrasonic waves to a treatment area through the treatment window. The heat-transferring surface is intimately surrounding the treatment window, and thermally contacted with the treatment area. The cooling mechanism is configured to discharge heat generated at the treatment area outside of the ultrasonic device by thermally contacting the heat-transferring surface. During the treatment process of the ultrasonic treatment device, the temperature of the treatment area will rise. When the surface of the skin at the treatment area rises to a certain temperature, the surface of the skin at the treatment area will be burned. In this solution, a heat-transferring surface is provided at the end face of the ultrasonic treatment tip, and a cooling mechanism contacts with the heat-transferring surface. The heat-transferring surface will contact with the treatment area during treatment, and the heat-transferring surface will take away the heat at the treatment area. The cooling mechanism will also cool down the heat-transferring surface to avoid excessively high temperature of the skin surface of the treatment area and burn the skin, or to avoid the temperature of the heat-transferring surface being too high and scalding the treatment area due to untimely heat dissipation. It can be seen that this solution can transfer the heat from the treatment area in time to avoid burning the treatment area.

BRIEF DESCRIPTION OF THE DRAWINGS

To more clearly illustrate technical solutions in the embodiments of the present application or the related art, the following will briefly introduce the drawings that need to be used in the description of the embodiments or the related art. Obviously, the drawings in the following description are only some embodiments of the present application. For those skilled in the art, without creative effort, other drawings can be obtained according to the structures shown in these drawings.

Figure 1:
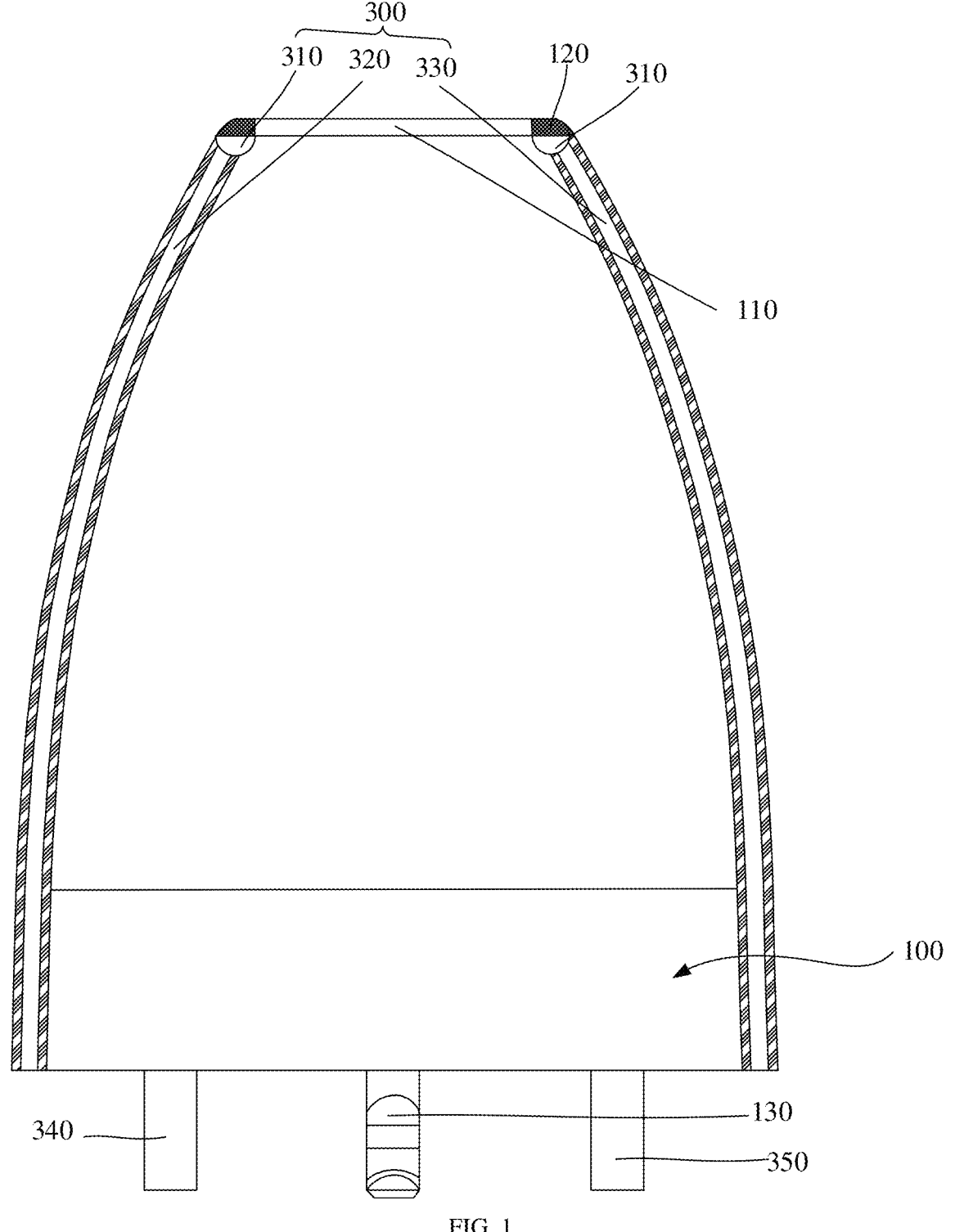
FIG. 1 is a schematic cross-sectional structural diagram of the ultrasonic treatment tip of the ultrasonic treatment device according to a first embodiment of the present application from one perspective.

The realization of the objective, functional characteristics, and advantages of the present application are further described with reference to the accompanying drawings.

DETAILED DESCRIPTION OF THE EMBODIMENTS

The technical solutions of the embodiments of the present application will be described in detail below with reference to the accompanying drawings. It is obvious that the embodiments described are only some rather than all of the embodiments of the present application. All other embodiments obtained by those skilled in the art based on the embodiments of the present application without creative efforts shall fall within the claimed scope of the present application.

It should be noted that all the directional indications (such as up, down, left, right, front, rear . . . ) in the embodiments of the present application are only used to explain the relative positional relationship, movement, or the like of the components in a certain posture (as shown in the drawings). If the specific posture changes, the directional indication will change accordingly.

In the present application, unless otherwise clearly specified and limited, the terms "connected", "fixed", etc. should be interpreted broadly. For example, "fixed" can be a fixed connection, a detachable connection, or a whole; can be a mechanical connection or an electrical connection; may be directly connected, or indirectly connected through an intermediate medium, and may be the internal communication between two elements or the interaction relationship between two elements, unless specifically defined otherwise. For those skilled in the art, the specific meaning of the above-mentioned terms in the present application can be understood according to specific circumstances.

Besides, the descriptions associated with, e.g., "first" and "second," in the present application are merely for descriptive purposes, and cannot be understood as indicating or suggesting relative importance or impliedly indicating the number of the indicated technical feature. Therefore, the feature associated with "first" or "second" can expressly or impliedly include at least one such feature. Further, if "and/or" appears throughout the text, it includes three parallel schemes. Taking "A and/or B" as an example, it includes the scheme A, or the scheme B, or the scheme that the scheme A and the scheme B satisfy at the same time. In addition, the technical solutions of the various embodiments can be combined with each other, but the combinations must be based on the realization of those skilled in the art. When the combination of technical solutions is contradictory or cannot be achieved, it should be considered that such a combination of technical solutions does not exist, nor does it fall within the scope of the present application.

The present application proposes an ultrasonic treatment device.

As shown in FIG. 1 to FIG. 4, in one embodiment of the present application, the ultrasonic treatment device includes an ultrasonic treatment tip 100 and a cooling mechanism. The ultrasonic treatment tip 100 includes a sealed cavity, a sound-transferring medium disposed inside the sealed cavity, a treatment window 110 and a heat-transferring surface 120. The ultrasonic treatment tip 100 is configured for outputting ultrasonic waves to a treatment area through the treatment window 110. The heat-transferring surface 120 is intimately surrounding the treatment window 110, and thermally contacted with the treatment area. The cooling mechanism is configured to discharge heat generated at the treatment area outside of the ultrasonic device by thermally contacting the heat-transferring surface 120.

In an embodiment, during the treatment process of the ultrasonic treatment device, the temperature of the treatment area will rise. When the surface of the skin at the treatment area rises to a certain temperature, the surface of the skin at the treatment area will be burned. In this solution, a heat-transferring surface 120 is provided at the end face of the ultrasonic treatment tip, and a cooling mechanism contacts with the heat-transferring surface 120. The heat-transferring surface 120 will contact with the treatment area during treatment, and the heat-transferring surface 120 will take away the heat at the treatment area. The cooling mechanism will also cool down the heat-transferring surface 120 to avoid excessively high temperature of the skin surface of the treatment area and burn the skin, or to avoid the temperature of the heat-transferring surface being too high and scalding the treatment area due to untimely heat dissipation. It can be seen that this solution can transfer the heat from the treatment area in time to avoid burning the treatment area.

Figure 4:
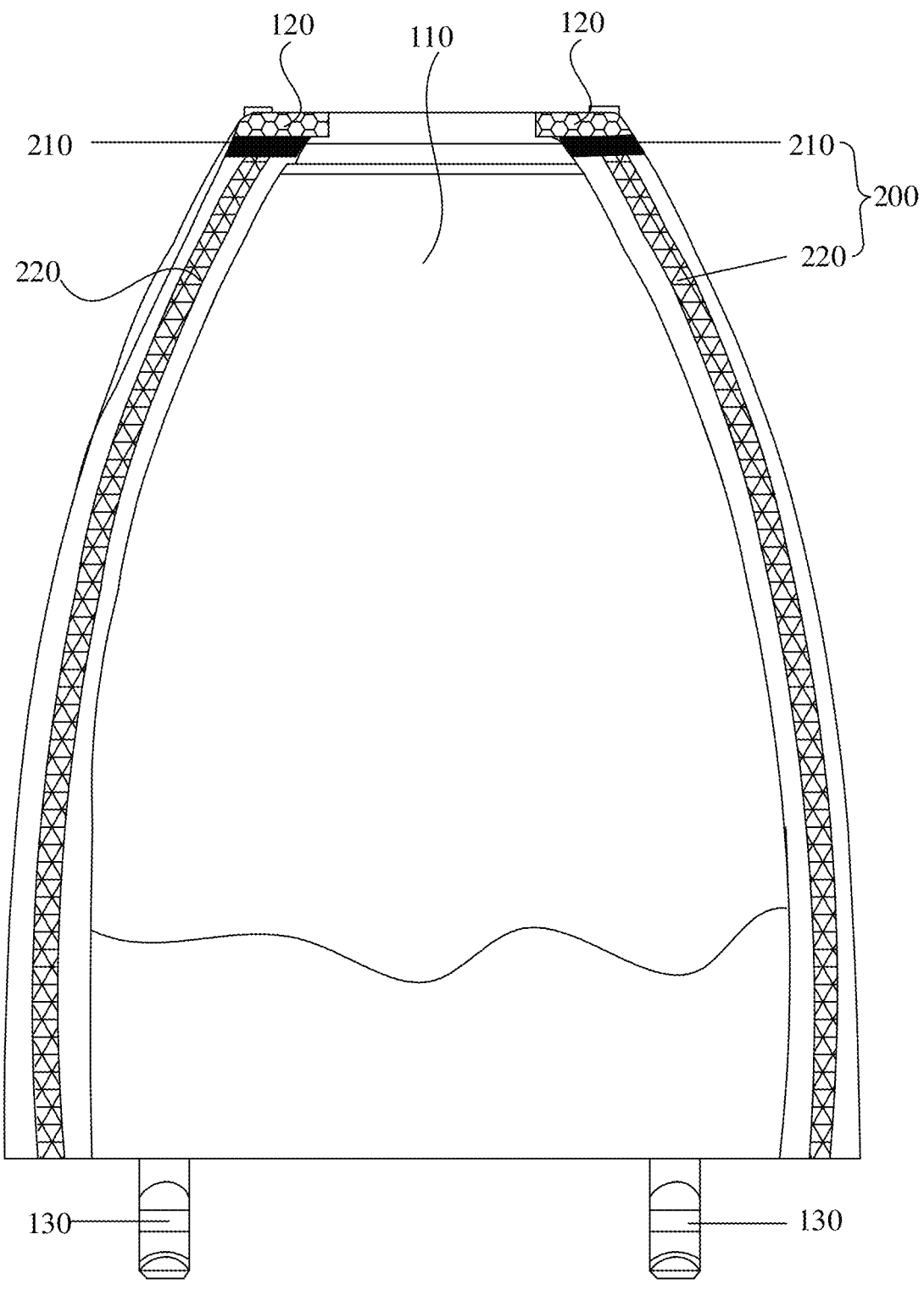
FIG. 4 is a schematic cross-sectional structural diagram of the ultrasonic treatment tip of the ultrasonic treatment device according to a second embodiment of the present application from one perspective.
Figure 5:
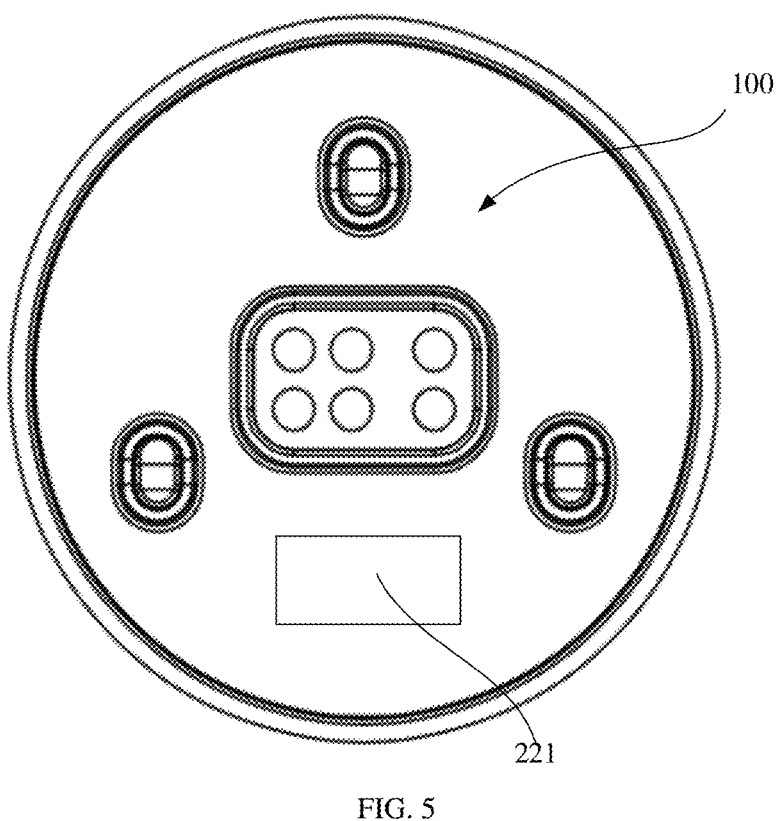
FIG. 5 is a schematic cross-sectional structural diagram of the ultrasonic treatment tip of the ultrasonic treatment device in FIG. 4 from another perspective.

As shown in FIG. 4 and FIG. 5, in one embodiment, the cooling mechanism includes a semiconductor cooling assembly 200, and the semiconductor cooling assembly 200 includes a semiconductor cooling sheet 210, a heat-transferring member 220 and a heat-dissipating member; a cold end of the semiconductor cooling sheet 210 is tightly attached with the heat-transferring surface 120, and a hot end of the semiconductor cooling sheet 210 is tightly attached with the heat-transferring member 220; a heat exchange end of the heat-transferring member 220 away from the semiconductor cooling sheet 210 is connected to the heat-dissipating member. It can be understood that when in use, the temperature of the treatment area will be successively transferred along the heat-transferring surface 120, the semiconductor cooling sheet 210, the heat-transferring member 220 and the heat-dissipating member, thereby dissipating heat from the ultrasonic treatment device. Since the cooling surface of the semiconductor cooling sheet 210 is directly connected to the heat-transferring surface 120, the low temperature generated by the cooling surface of the semiconductor cooling sheet 210 is balanced due to the heat transferred from the treatment area by the heat-transferring surface 120, and an excellent cooling effect is thus produced.

In an embodiment, the heat-dissipating member includes a heat-dissipating sheet. Since the heat-dissipating sheet has efficient heat dissipation performance, strong anti-corrosion performance, and high cost performance, the service life of the heat-dissipating member can be increased. In an embodiment, the heat-dissipating sheet may be a metal heat-dissipating sheet or a ceramic heat-dissipating sheet, and the heat-dissipating member is not specifically limited here.

Further, the ultrasonic treatment device also includes a handle. The handle is connected to the connection end of the ultrasonic treatment tip 100 away from the heat-transferring surface 120, and the heat-dissipating member is provided at the handle. The heat exchange end 221 is provided at the connection end, and the heat exchange end 221 abuts against the heat-dissipating member. It can be understood that the heat-dissipating member is installed at the handle, so that the overall installation space of the cooling mechanism can be larger, which is convenient for installation and operation. Of course, the present application is not limited to this. In other embodiments, the heat-dissipating member can also be provided at one end of the ultrasonic treatment tip 100 away from the heat-transferring surface 120.

In an embodiment, the semiconductor cooling assembly 200 further includes a heat-dissipating fan, which is provided at one side of the heat-dissipating member. The heat-transferring member 220 can transfer the heat energy generated by the semiconductor cooling sheet 210 to the heat-dissipating member provided in the handle, and then the heat-dissipating fan can be used to blow the heat of the heat-dissipating member out of the ultrasonic treatment device, thereby increasing the heat dissipation efficiency.

In the second embodiment, the cooling mechanism includes a semiconductor cooling assembly. The semiconductor cooling assembly includes a semiconductor cooling sheet. The cold end of the semiconductor cooling sheet is tightly attached with the heat-transferring surface, and the hot end of the semiconductor cooling sheet is tightly attached with the sealed cavity. It can be understood that, for such a semiconductor cooling assembly structure, the existing sound-transferring medium can be used to spread the heat of the semiconductor cooling sheet, thereby saving the heat-transferring members and saving production costs.

Figure 2:
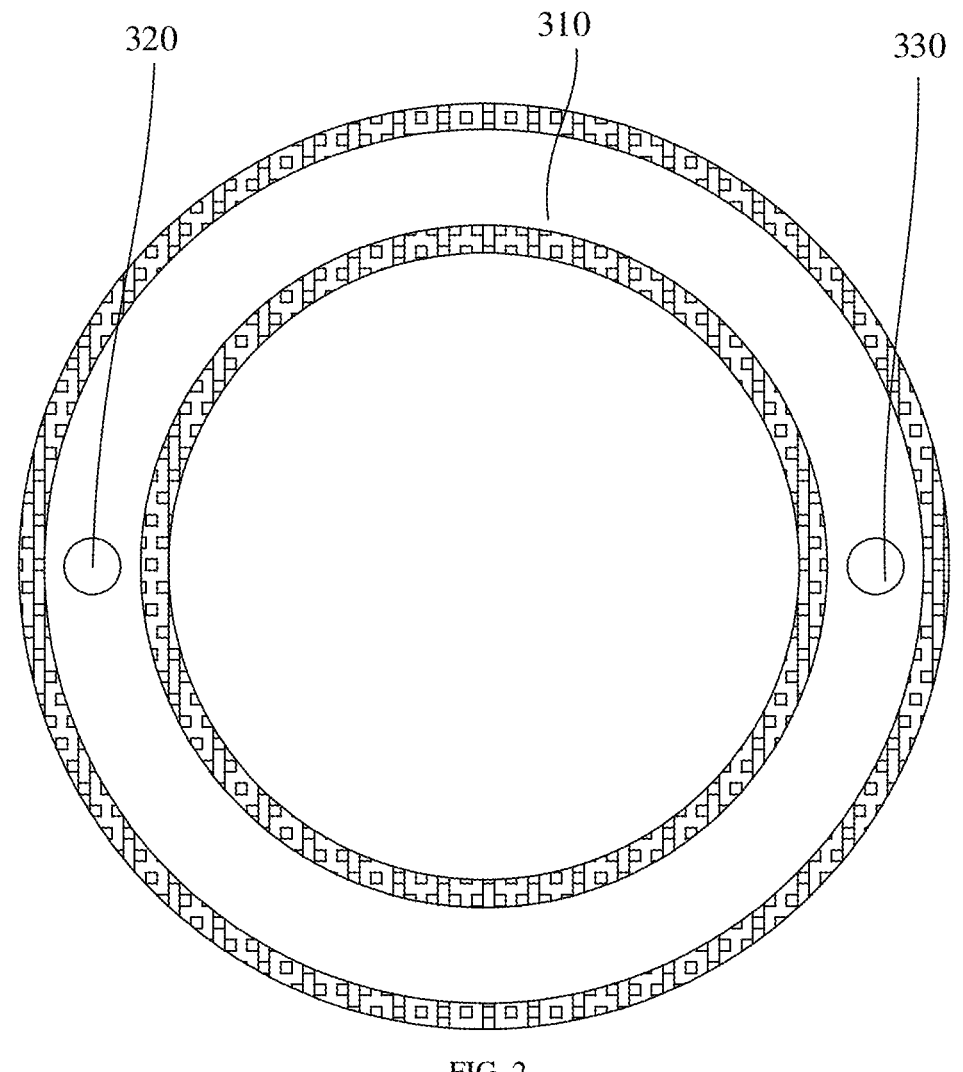
FIG. 2 is a schematic cross-sectional structural diagram of the ultrasonic treatment tip of the ultrasonic treatment device in FIG. 1 from another perspective.
Figure 3:
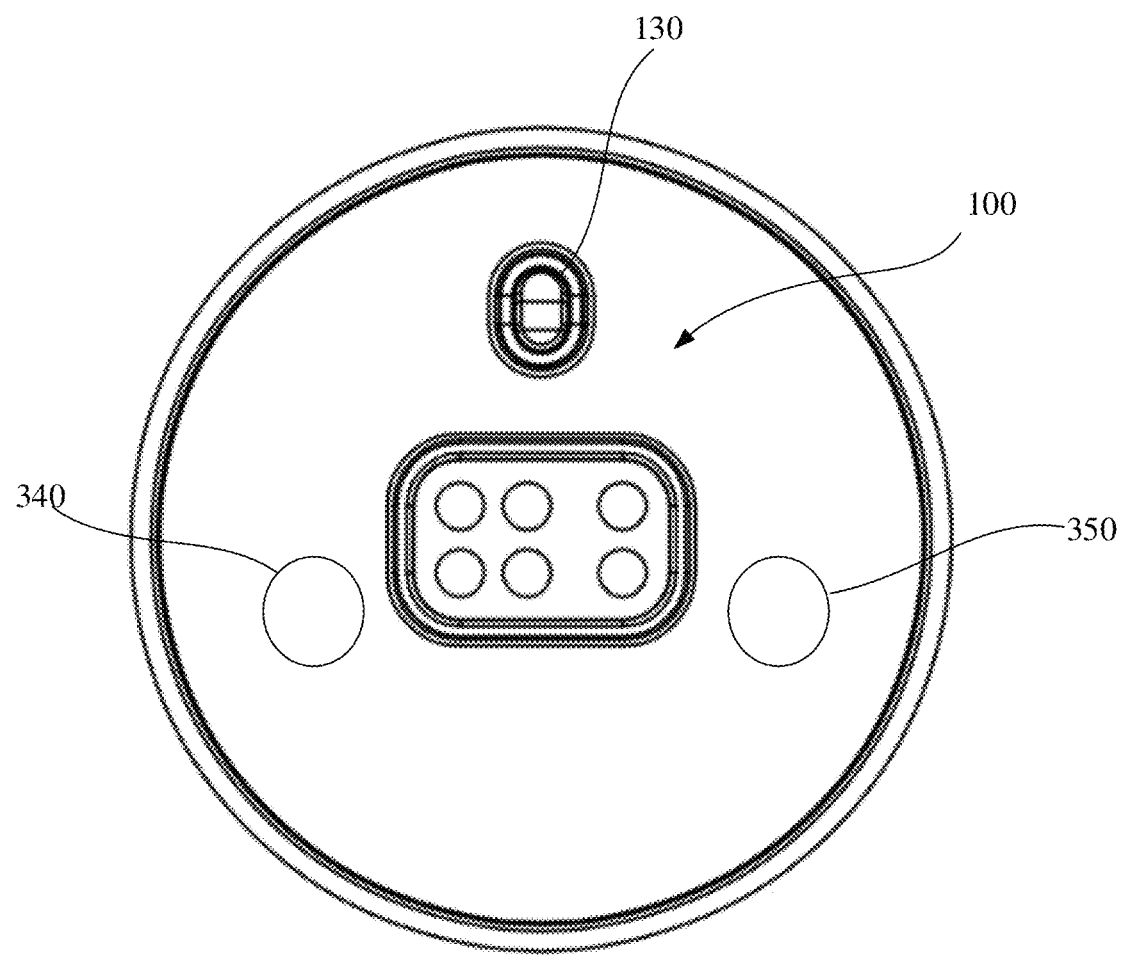
FIG. 3 is yet a schematic cross-sectional structural diagram of the ultrasonic treatment tip of the ultrasonic treatment device in FIG. 1 from another perspective.

As shown in FIG. 1 to FIG. 3, in an embodiment, the cooling mechanism includes a water cooling assembly 300. The water cooling assembly 300 includes a water cooling cavity 310, a water inlet channel 320 and a water outlet channel 330. The water cooling cavity 310 is provided inside the shell of the ultrasonic treatment tip 100 and is provided close to the heat-transferring surface 120. The water inlet channel 320 is communicated with the water cooling cavity 310, and the water outlet channel 330 is communicated with the water cooling cavity 310. During use, when circulating water enters the water cooling cavity 310 through the water inlet channel 320, the heat transferred by the heat-transferring surface 120 from the treatment area is carried to the water outlet channel 330 on the other side by the circulating water flow and is discharged, thereby quickly and effectively dissipating heat at the treatment area. In this method of directly cooling the heat of the heat-transferring surface 120 through circulating water cooling has a good effect.

In an embodiment, the water inlet channel 320 and the water outlet channel 330 are provided at the inner side of the shell of the ultrasonic treatment tip 100. It can be understood that the water inlet channel 320 and the water outlet channel 330 are provided at the inner side of the shell of the ultrasonic treatment tip 100, which can avoid the water inlet channel 320 and the water outlet channel 330 being externally provided, thereby avoiding the water inlet channel 320 and the water outlet channel 330 from interfering with the hands of the user during the treatment of the ultrasonic treatment device. Of course, the present application is not limited to this. In other embodiments, the water inlet channel 320 and the water outlet channel 330 can also be provided at the outer side of the shell of the ultrasonic treatment tip 100.

Furthermore, the ultrasonic treatment device further includes a handle. The connection end of the ultrasonic treatment tip 100 away from the heat-transferring surface 120 is convexly provided with a hook 130, a water inlet pipe section 340 and a water outlet pipe section 350. The water inlet pipe section 340 is communicated with the water inlet channel 320, and the water outlet pipe section 350 is communicated with the water outlet channel 350. The handle of the ultrasonic treatment device is configured to snap on the hook 130 to connect the connection end of the ultrasonic treatment tip 100. It can be understood that the installation process of snapping is very simple, generally only one pushing action is required, and no rotational movement or product positioning work before installation is required. The quick and simple operation can speed up the installation speed of the ultrasonic treatment device. Of course, the present application is not limited to this. In other embodiments, the water inlet pipe section 340 and the water outlet pipe section 350 may not be convexly provided at the end face of the connection end of the ultrasonic treatment tip 100 away from the heat-transferring surface 120.

Furthermore, the connection end of the ultrasonic treatment tip 100 away from the heat-transferring surface 120 is convexly provided with a hook 130, a water inlet pipe section 340 and a water outlet pipe section 350, which can avoid mistakes when the ultrasonic treatment tip 100 is installed with the handle.

Further, the water cooling assembly 300 also includes a water tank and a water pump. The water tank and the water pump are provided at the handle. The water pump, the water tank, the water inlet channel 320, the water outlet channel 330 and the water cooling cavity 310 are communicated with each to form a water cooling channel.

Furthermore, the water inlet channel 320 and the water outlet channel 330 are provided away from each other, in this way, the circulating water can run along the cavity path of the water cooling cavity 310, avoiding the blind angle of the water cooling cavity 310 where the circulating water cannot run, thereby increasing the heat dissipation efficiency of the heat-transferring surface 120. Of course, the present application is not limited to this. In other embodiments, the water inlet channel 320 and the water outlet channel 330 can also be provided close to each other, but it is necessary to set the water inlet channel 320 and the water outlet channel 330 inside the water cooling cavity 310 and set a partition between the water inlet channel 320 and the water outlet channel 330.

Figure 6:
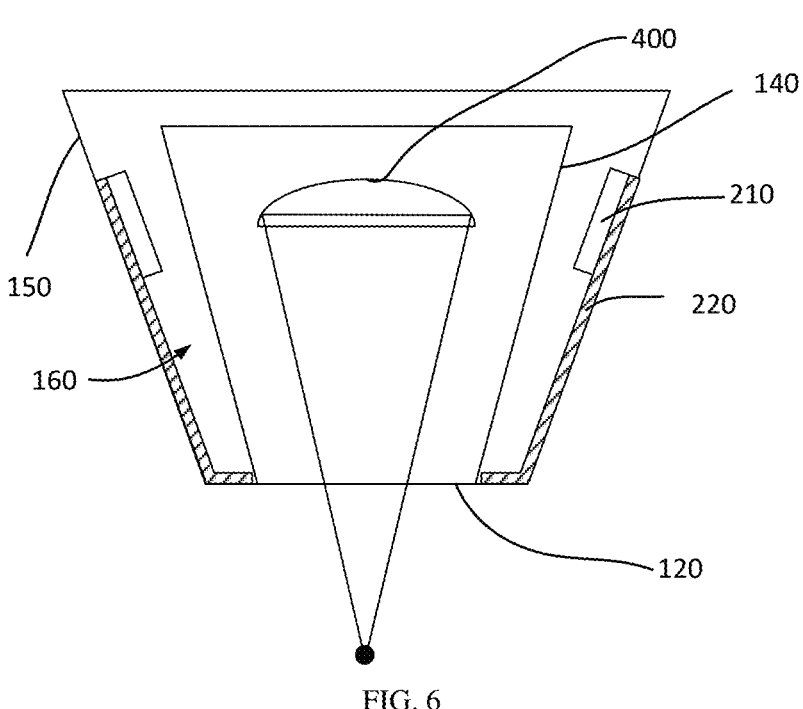
FIG. 6 is a schematic cross-sectional structural diagram of the ultrasonic treatment tip of the ultrasonic treatment device according to a third embodiment of the present application.

In the embodiment shown in FIG. 6, the cooling mechanism includes a semiconductor cooling sheet 210 and a heat-transferring member 220. One end of the heat-transferring member 220 is attached with the semiconductor cooling sheet 210, and the other end of the heat-transferring member 220 is attached with the heat-transferring surface 120. The semiconductor cooling sheet 210 is thermally connected to the heat-transferring surface 120 through the heat-transferring member 220. The working current of the semiconductor cooling sheet 210 includes a first direction current and a second direction current. The current direction of the first direction current is opposite to the current direction of the second direction current. When the working current of the semiconductor cooling sheet 210 is the first direction current, the end of the semiconductor cooling sheet 210 tightly attached with the heat-transferring member 220 is the hot end. When the working current of the semiconductor cooling sheet 210 is the second direction current, the end of the semiconductor cooling sheet 210 tightly attached with the heat-transferring member 220 is the cold end.

According to the characteristics of the semiconductor cooling sheet 210, after electrifying direct current, the semiconductor cooling sheet 210 will absorb heat at one end and release heat at the other end, forming cold and hot ends. The ultrasonic treatment device can switch the cold end and the hot end of the semiconductor cooling sheet 210 by controlling the current direction inputted into the semiconductor cooling sheet 210, thereby controlling the cooling state and the heating state of the cooling mechanism.

In an embodiment, during the startup phase of the ultrasonic treatment device, the working current of the semiconductor cooling sheet 210 is controlled to be a first direction current. In this case, the end of the semiconductor cooling sheet 210 that is tightly attached with the heat-transferring member 220 is the hot end, and the end away from the heat-transferring member 220 is the cold end. The semiconductor cooling sheet 210 is in a heating state. The heat-transferring member 220 transfers the high temperature of the hot end of the semiconductor cooling sheet 210 to the heat-transferring surface 120, thereby heating the skin surface and raising the temperature of the skin, so that the treatment period quickly transcends the early heating stage and shortens the preheating time. In the startup phase, the heating function of the semiconductor cooling sheet 210 and the ultrasonic emission function of the ultrasonic treatment device can be turned on simultaneously to improve the treatment efficiency. In another embodiment of the present application, only the heating function of the semiconductor cooling sheet can be turned on in the startup phase, and the treatment parameters (such as temperature and impedance) of the target tissue can be detected simultaneously. After the treatment parameter reaches a certain threshold, the ultrasonic emission function of the ultrasonic treatment device can be turned on to avoid obvious pain caused by excessive energy inputted in the early stage.

The control members for the semiconductor cooling sheet 210 can be integrated into the control system of the ultrasonic treatment device, or the control on the semiconductor cooling sheet 210 can be achieved separately through a switch. In one embodiment, on and off states of the semiconductor cooling sheet 210 are switchable by a switch provided in the ultrasonic treatment device. In another optional embodiment, the ultrasonic treatment device includes a switch and a power supply that can separately control the semiconductor cooling sheet 210 to be turned on and/or off. Therefore, the heating function or the cooling function of the ultrasonic treatment device can be used separately without using the ultrasonic energy, such as warming or cold compressing without additional device after treatment. The switch here can be a physical switch (such as a button on the treatment device) or a switch on the control interface, such as a control button on the user interface of the treatment device host.

During the treatment stage of the ultrasonic treatment device, when the temperature of the heat-transferring surface 120 is higher than the preset temperature range, the working current inputted to the semiconductor cooling sheet 210 is controlled to be a second direction current. In this case, the end of the semiconductor cooling sheet 210 that is tightly attached with the heat-transferring member 220 is the cold end, and the end away from the heat-transferring member 220 is the hot end. The semiconductor cooling sheet 210 is in a cooling state, and the heat-transferring member 220 transfers the low temperature of the cold end of the semiconductor cooling sheet 210 to the heat-transferring surface 120, thereby timely cooling the heat-transferring surface 120. When the temperature of the treatment area is lower than the preset temperature range, the working current inputted to the semiconductor cooling sheet 210 is controlled to be the first direction current, and the semiconductor cooling sheet 210 is switched to the heating state, thereby controlling the temperature of the treated skin within the preset temperature range.

In summary, for this embodiment, by controlling the current direction inputted to the semiconductor cooling sheet 210, the cooling state and the heating state of the semiconductor cooling sheet 210 can be changed, thereby controlling the temperature of the heat-transferring surface 120 within the preset temperature range, avoiding the phenomenon of the treatment temperature being too high or too low, thereby shortening the treatment time while ensuring the treatment effect and improving the comfort of the treatment.

In this case, the cooling mechanism may further include a heat-dissipating member, which is provided at the side of the semiconductor cooling sheet 210 away from the heat-transferring member 220, and is provided in heat-transferring contact with the semiconductor cooling sheet 210, for dissipating heat from the semiconductor cooling sheet 210. For example, the heat-dissipating member may be a heat sink fin, which may be made of metal or ceramic. Or the heat-dissipating member may be a heat-dissipating pipe, in which a refrigerant may flow, and the refrigerant circulates in the heat-dissipating pipe to improve the heat dissipation effect. Or the heat-dissipating member may be a heat-dissipating fan.

It should be noted that the heat-transferring surface 120 is provided with a sound-transmitting area located in the central area and an outer annular area surrounding the sound-transmitting area. In one embodiment, the heat-transferring member 220 can be in an annular shape and is attached to the outer annular area. On the one hand, it ensures a sufficient contact area between the heat-transferring member 220 and the heat-transferring surface 120, and on the other hand, it meets the requirements of sound wave penetration of the ultrasonic transducer. In another embodiment, the heat-transferring member can also be distributed discretely, such as a plurality of discrete heat-transferring points, a plurality of discrete heat-transferring arc structures, and the like. In another embodiment, the heat-transferring member 220 can include a first heat-transferring sheet and a second heat-transferring sheet. The first heat-transferring sheet is in an annular shape and is attached to the inner wall of the shell 150. The second heat-transferring sheet is in an annular shape and is provided at one end of the first heat-transferring sheet facing the heat-transferring surface 120, and is attached to the outer annular area. In this embodiment, the heat-transferring surface of the heat-transferring member 220 can be increased, thereby increasing the heat transfer efficiency.

In the embodiment of the ultrasonic treatment device, as shown in FIG. 6, the ultrasonic treatment tip 10 includes an outer shell 150 and an inner shell 140. The inner shell 140 is provided in the chamber of the outer shell 150, and an ultrasonic cavity 160 is formed in the inner shell 140. An ultrasonic transducer unit is provided in the ultrasonic cavity 160. The ultrasonic transducer unit is immersed in the sound-transferring medium and emits ultrasonic waves toward the treatment window 110. The sound-transferring medium may be degassed water or glycerin, and no specific limitation is made to the sound-transferring medium. The ultrasonic waves emitted by the ultrasonic transducer unit pass through the treatment window 110 and act on the treatment skin.

The outer wall of the inner shell 140 and the inner wall of the outer shell 150 are spaced apart to form a heat-insulating cavity 13, and a heat-insulating member (not shown) is provided in the heat-insulating cavity 13. For example, the heat-insulating member is a heat-insulating film, and the heat-insulating film is circumferentially coated on the outer peripheral surface of the inner shell 140. The heat-insulating film can be made of heat-insulating materials, such as the glass wool, and the vacuum insulation board.

It is not difficult to understand that the semiconductor cooling sheet 210 and the heat-transferring member 220 will radiate heat to the heat-insulating cavity 13, so that the sound-transferring medium in the ultrasonic cavity 160 will also be affected by the heat. The setting of the heat-insulating member can reduce the heat exchange between the sound-transferring medium and the heat-insulating cavity 13.

The ultrasonic transducer unit may include a single ultrasonic transducer 400, which is movable in an ultrasonic cavity 160 and emits ultrasonic waves toward a heat-transferring surface 120. If a sliding track is provided in the ultrasonic cavity 160, the ultrasonic transducer 400 is slidably connected to the inner shell 140 through the sliding track, thereby realizing position movement. Each ultrasonic transducer 400 has a preset travel track, and can reciprocate between the starting point and the ending point of each travel, thereby radiating a larger heat-transferring area, reducing the number of sliding of the ultrasonic treatment tip 10.

In an embodiment, the ultrasonic transducer unit may include a plurality of ultrasonic transducers 400, and the plurality of ultrasonic transducers 400 are installed in the ultrasonic cavity 160 in an array and will emit ultrasonic waves toward the heat-transferring surface 120. The array arrangement of the ultrasonic transducers 400 may also increase the treatment area and/or increase the treatment energy. The array of the ultrasonic transducers may also be a phased array, and electronic scanning focusing is achieved by controlling the electrical signal phase of the transducer units constituting the ultrasonic transducer.

In addition, the ultrasonic treatment tip also includes a controller and a temperature sensor installed thereon that can sense the temperature of the heat-transferring surface. The temperature sensor is electrically connected to the controller to feedback the detected temperature to the controller in real time, and the controller is used to control the cooling mechanism. It can be understood that the controller is used to control the semiconductor cooling sheet 210 or the flow rate of the circulating water. By providing the temperature sensor and the controller, the heat transfer efficiency of the cooling mechanism to the heat-transferring surface 120 can be adjusted conveniently, thereby avoiding the temperature of the heat-transferring surface 120 being fluctuated sharply, thereby increasing the comfort of use.

The temperature sensor is provided with a first temperature threshold and a second temperature threshold, and the second temperature threshold is greater than the first temperature threshold. When the temperature sensor detects that the real time temperature of the heat-transferring surface 120 fall within the first threshold and the second threshold, the ultrasonic treatment device is in a normal working state. When the temperature sensor detects that the real time temperature of the heat-transferring surface 120 is greater than the second temperature threshold, the controller controls the working current inputted to the semiconductor cooling sheet 210 to be the second direction current, controls the semiconductor cooling sheet 210 to cool, and thus timely cooling the heat-transferring surface 120. When the temperature sensor detects that the real time temperature of the heat-transferring surface 120 is less than the first temperature threshold, the controller controls the working current inputted to the semiconductor cooling sheet 210 to be the first direction current during at least partial working period of the ultrasonic treatment device, controls the semiconductor cooling sheet 210 to heat, thereby heating the heat-transferring surface 120.

The present application also proposes a method for controlling the ultrasonic treatment device, which includes the following operations: during at least partial working period of the ultrasonic treatment device, controlling a working current of the semiconductor cooling sheet to be a first direction current, to make ultrasonic energy and heat of the semiconductor cooling sheet at least partially overlapped and acted on a same target tissue.

For example, the ultrasonic treatment device includes a first working period (start-up phase) in the early stage, a second working period (treatment phase) for emitting ultrasonic energy, and a third working period (cooling phase) after emitting ultrasonic energy. In the first working period of the ultrasonic treatment device, the working current of the semiconductor cooling sheet is controlled to be the first direction current, and the semiconductor cooling sheet 210 is heated, so that the treatment period quickly crosses the early heating phase and improves the treatment efficiency. In the third working period of the ultrasonic treatment device, the treatment process of the ultrasonic treatment device is completed, but there is still a high residual temperature at the target tissue. In this case, the working current of the semiconductor cooling sheet is controlled to be the second direction current, and the semiconductor cooling sheet 210 will cool the target tissue and improve the treatment comfort.

The above-mentioned first working period and the third working period are not necessary for the present application. In addition to the second working period, the entire treatment process may include only one, all or none of the first working period and the second working period.

In another embodiment, in the first working period, the working current of the semiconductor cooling sheet is controlled to be the second direction current. In this scheme, the skin can be cooled before ultrasonic energy is received, the pain nerves can be paralyzed, and the pain can be reduced.

In the third working period, the working current of the semiconductor cooling sheet can also be controlled to be the first direction current. In this scheme, the skin can be continuously heated after ultrasonic energy is received, uniform heat dispersion can be performed, thereby improving the treatment effect.

In one embodiment, in the first working period (start-up phase) and the second working period (treatment phase) of the ultrasonic treatment device, the heating function of the semiconductor cooling sheet 210 and the ultrasonic emission function of the ultrasonic treatment device are turned on simultaneously to improve the treatment efficiency.

In another embodiment, only the heating function of the semiconductor cooling sheet is turned on during the startup phase, and the treatment parameters of the target tissue (such as temperature and impedance) can be detected simultaneously. When a certain threshold is reached, the ultrasonic treatment device will start to emit ultrasound, thus avoiding obvious pain due to excessive energy input in the early stage.

In one embodiment of the method, in a process of emitting ultrasonic energy, the ultrasonic treatment device performs the following operations during the process of emitting ultrasonic energy:

obtaining a real time treatment parameter of a target tissue;

determining whether the real time treatment parameter is less than a first treatment parameter;

in response to that the real time treatment parameter is less than the first treatment parameter, controlling the working current of the semiconductor cooling sheet to be the first direction current;

in response to that the real time treatment parameter is not less than the first treatment parameter, determining whether the real time treatment parameter is greater than a second treatment parameter;

in response to that the real time treatment parameter is greater than the second treatment parameter, controlling the working current of the semiconductor cooling sheet to be the second direction current;

in response to that the real time treatment parameter is not greater than the second treatment parameter, controlling the working current of the semiconductor cooling sheet to be the first direction current.

In an embodiment, the real time treatment parameter includes a real time temperature of the treatment area. The temperature sensor detects the real time temperature of the treatment area, and transmit the real time temperature of the treatment area the controller.

The current direction of the first direction current is opposite to the current direction of the second direction current. The real time treatment parameter of the target tissue includes but is not limited to temperature parameters and image parameters, such as the surface temperature, the central temperature, the color, the impedance, and the like of the target tissue. In the startup phase of the ultrasonic treatment device, the real time treatment parameter of the target tissue is less than the first treatment parameter, the working current of the semiconductor cooling sheet is the first direction current, and the semiconductor cooling sheet is in a heating state. When the real time treatment parameter of the target tissue reaches the first treatment parameter, the ultrasonic treatment device enters the second working period (working phase). In this case, in order to prevent the real time treatment parameter of the target tissue from being too high or too low during the treatment, it is necessary to monitor whether the real time treatment parameter of the target tissue is greater than the second treatment parameter. If the real time treatment parameter of the target tissue is greater than the second treatment parameter, it means that the ultrasonic energy temperature is too high. In this case, the working current of the semiconductor cooling sheet is controlled to be the second direction current, and the semiconductor cooling sheet will perform cooling. If the real time treatment parameter of the target tissue is not greater than the second treatment parameter, it means that the ultrasonic energy temperature is too low. In this case, the working current of the semiconductor cooling sheet is controlled to be the first direction current, and the semiconductor cooling sheet will start heating.

In one embodiment of the method, the ultrasonic treatment device includes a first working mode and a second working mode. When the ultrasonic treatment device is in the first working mode, the ultrasonic treatment device emits ultrasonic energy to the target tissue, and the working current of the semiconductor cooling sheet is the first direction current. When the ultrasonic treatment device is in the second working mode, the ultrasonic treatment device emits ultrasonic energy to the target tissue, and the working current of the semiconductor cooling sheet is the second direction current. The working sequence of the ultrasonic treatment device only includes the first working sequence, or at least includes the first working sequence and the second working sequence. In the first working sequence of the ultrasonic treatment device, the ultrasonic treatment device is controlled to enter the first working mode, and in the second working sequence of the ultrasonic treatment device, the ultrasonic treatment device is controlled to enter the second working mode.

That is, in one embodiment, the ultrasonic treatment device is only in the first working mode, and performs heating with a semiconductor cooling sheet and superimposed ultrasonic treatment, thereby achieving the most efficient heat accumulation to complete treatment. In another embodiment, the ultrasonic treatment device is first in the first working mode, and then in the second working mode. First, the optimal treatment temperature range can be achieved as quickly as possible by superimposing heating and ultrasonic treatment, and then performs cooling control to reduce pain, taking into account both efficiency and comfort.

In this embodiment, the ultrasonic treatment device program is set with a first working mode and a second working mode. In the first working mode, while the ultrasonic treatment device emits ultrasonic energy outward, the first direction current flows into the semiconductor cooling sheet, that is, the heating function of the semiconductor cooling sheet 210 and the ultrasonic emission function of the ultrasonic treatment device are turned on simultaneously. In the second working mode, while the ultrasonic treatment device emits ultrasonic energy outward, a second direction current flows into the semiconductor cooling sheet, that is, the cooling function of the semiconductor cooling sheet 210 and the ultrasonic emission function of the ultrasonic treatment device are turned on simultaneously. In this case, the first working mode and the second working mode of the ultrasonic treatment device can be manually switched; or, the ultrasonic treatment device is set beforehand to have a first working sequence [0, T1] and a second working sequence [T1, T2]. When the clock parameter T obtained by the ultrasonic treatment device is less than T1, the controller automatically controls the ultrasonic treatment device to enter the first working mode. When the clock parameter T obtained by the ultrasonic treatment device is greater than T1, the controller automatically controls the ultrasonic treatment device to enter the second working mode. Of course, the ultrasonic treatment device is also provided with an automatic mode and a manual mode, which can make the use of the ultrasonic treatment device more flexible. For example, the ultrasonic treatment device can be controlled to complete the entire treatment in only a single first working mode or a second working mode.

The ultrasonic treatment device further performs the following operations in the third working period: determining whether a real time temperature of a target tissue is lower than a first temperature threshold; in response to that the real time temperature of the target tissue is lower than the first temperature threshold, cutting off or reducing the working current of the semiconductor cooling sheet.

The above are only some embodiments of the present application, and do not limit the scope of the present application thereto. Under the concept of this application, any equivalent structural transformation made according to the description and drawings of the present application, or direct/indirect application in other related technical fields shall fall within the claimed scope of the present application.

What is claimed is:

1. An ultrasonic treatment device, comprising an ultrasonic treatment tip and a cooling or heating mechanism, wherein the ultrasonic treatment tip comprises a sealed cavity, a sound-transferring medium disposed inside the sealed cavity, a treatment window and a heat-transferring surface;

the ultrasonic treatment tip is configured for outputting ultrasonic waves to a treatment area through the treatment window;

the heat-transferring surface is intimately surrounding the treatment window, and thermally contacted with the treatment area; and the cooling or heating mechanism is configured to discharge heat generated at the treatment area outside of the ultrasonic device by thermally contacting the heat-transferring surface or generate heat at least partially overlapped with heat of the ultrasonic waves on a same target tissue, wherein the cooling or heating mechanism comprises a semiconductor assembly, and the semiconductor assembly comprises a semiconductor sheet, a heat-transferring member and a heat-dissipating member; a cold end of the semiconductor sheet is tightly attached with the heat-transferring surface, and a hot end of the semiconductor sheet is tightly attached with the heat-transferring member; a heat exchange end of the heat-transferring member away from the semiconductor sheet is connected to the heat-dissipating member.

2. The ultrasonic treatment device according to claim 1, wherein the heat-dissipating member is configured as a heat-dissipating sheet.

3. The ultrasonic treatment device according to claim 1, further comprising:

a handle;

wherein the handle is connected to a connection end of the ultrasonic treatment tip away from the heat-transferring surface, and the heat-dissipating member is disposed within the handle; the heat exchange end is provided at the connection end, and the heat exchange end is abutted against the heat-dissipating member.

4. The ultrasonic treatment device according to claim 3, wherein the semiconductor assembly further comprises a heat-dissipating fan, and the heat-dissipating fan is provided at one side of the heat-dissipating member.

5. The ultrasonic treatment device according to claim 1, wherein the cooling or heating mechanism comprises a semiconductor assembly, and the semiconductor assembly comprises a semiconductor sheet; a cold end of the semiconductor sheet is tightly attached with the heat-transferring surface, and a hot end of the semiconductor sheet is tightly attached with the sealed cavity.

6. The ultrasonic treatment device according to claim 1, wherein the cooling or heating mechanism comprises a water cooling assembly, and the water cooling assembly comprises a water cooling cavity, a water inlet channel and a water outlet channel; the water cooling cavity is provided inside a shell of the ultrasonic treatment tip and close to the heat-transferring surface; the water inlet channel is communicated with the water cooling cavity, and the water outlet channel is communicated with the water cooling cavity.

7. The ultrasonic treatment device according to claim 6, wherein the water inlet channel and the water outlet channel are provided at an inner side of the shell of the ultrasonic treatment tip.

8. The ultrasonic treatment device according to claim 7, further comprising:

a handle;

wherein a connection end of the ultrasonic treatment tip away from the heat-transferring surface is provided with a hook, a water inlet pipe section and a water outlet pipe section, and the water inlet pipe section is communicated with the water inlet channel; the water outlet pipe section is communicated with the water outlet channel, and the handle of the ultrasonic treatment device is configured to snap on the hook to connect the connection end of the ultrasonic treatment tip.

9. The ultrasonic treatment device according to claim 7, wherein the water inlet channel is disposed away from the water outlet channel.

10. The ultrasonic treatment device according to claim 1, wherein the cooling or heating mechanism comprises a heat-transferring member and a semiconductor sheet; one end of the heat-transferring member is attached with the semiconductor sheet, and the other end of the heat-transferring member is in thermal contact with the heat-transferring surface; the semiconductor sheet is thermally connected to the heat-transferring surface through the heat-transferring member; and on and off states of the semiconductor sheet are switchable by a switch provided in the ultrasonic treatment device, wherein a working current of the semiconductor sheet comprises a first direction current and a second direction current; the first direction current and the second direction current have opposite current directions; in response to that the working current of the semiconductor sheet is the first direction current, an end of the semiconductor sheet in attachment with the heat-transferring member is a hot end; and in response to that the working current of the semiconductor sheet is the second direction current, an end of the semiconductor sheet in attachment with the heat-transferring member is a cold end.

11. The ultrasonic treatment device according to claim 1, wherein the ultrasonic treatment tip is provided with an outer shell and an inner shell; the inner shell is provided in a cavity of the outer shell, and an ultrasonic cavity is provided in the inner shell; an ultrasonic transducer unit is provided in the ultrasonic cavity, and the ultrasonic transducer unit is configured to emit ultrasonic waves toward the treatment window; and the inner shell is provided with a first end face and a second end face opposite with each other; the treatment window is provided at the first end face, and the treatment window is tightly attached with the heat-transferring surface; an outer wall of the inner shell is spaced from an inner wall of the outer shell to form a heat-insulating cavity, and a heat-insulating member is disposed in the heat-insulating cavity.

12. The ultrasonic treatment device according to claim 11, wherein the ultrasonic transducer unit comprises one ultrasonic transducer, and the ultrasonic transducer is movable in the ultrasonic cavity and is configured to emit ultrasonic waves toward the heat-transferring surface.

13. The ultrasonic treatment device according to claim 11, wherein the ultrasonic transducer unit comprises a plurality 5 of ultrasonic transducers, and the plurality of ultrasonic transducers are provided in the ultrasonic cavity in an array and are configured to emit ultrasonic waves toward the heat-transferring surface.

14. The ultrasonic treatment device according to claim 1, 10 wherein the ultrasonic treatment tip further comprises a controller and a temperature sensor configured to sense temperature of the heat-transferring surface; the temperature sensor is electrically connected to the controller to feedback a detected temperature to the controller in real time, and the 15 controller is configured to control the cooling or heating mechanism.

*    *    *    *    *